US011944567B2

United States Patent
Karakaya et al.

(10) Patent No.: US 11,944,567 B2
(45) Date of Patent: Apr. 2, 2024

(54) SYSTEM FOR TREATING SNORING AMONG AT LEAST TWO USERS

(71) Applicant: KONINKLIJKE PHILIPS N.V., Eindhoven (NL)

(72) Inventors: Koray Karakaya, Eindhoven (NL); Steven Coughlin, Liverpool (GB); Benno Tieke, Oxted (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1046 days.

(21) Appl. No.: 16/471,308

(22) PCT Filed: Dec. 21, 2017

(86) PCT No.: PCT/EP2017/084219
§ 371 (c)(1),
(2) Date: Jun. 19, 2019

(87) PCT Pub. No.: WO2018/115351
PCT Pub. Date: Jun. 28, 2018

(65) Prior Publication Data
US 2020/0113727 A1    Apr. 16, 2020

Related U.S. Application Data

(60) Provisional application No. 62/438,485, filed on Dec. 23, 2016.

(51) Int. Cl.
*A61F 5/56* (2006.01)
*A47G 9/10* (2006.01)
*A61B 5/00* (2006.01)

(52) U.S. Cl.
CPC .......... *A61F 5/56* (2013.01); *A47G 9/10* (2013.01); *A61B 5/6887* (2013.01); *A61B 2562/0204* (2013.01)

(58) Field of Classification Search
CPC ....................................................... A61F 5/56
(Continued)

(56) References Cited

U.S. PATENT DOCUMENTS 6,386,201 B1    5/2002  Fard
2004/0139549 A1  7/2004  Mohrekesh et al.
(Continued)

FOREIGN PATENT DOCUMENTS

CN    2882572 Y      3/2007
DE    19535232 A1    3/1997
WO    2018033147 A1  2/2018

OTHER PUBLICATIONS

Raymond van Ee and Estrella Mena Benito, "Multisensory approach for the relief from tinnitus distress", PR-TN 2013/00257, Philips Research Technical Note, 2013.
(Continued)

*Primary Examiner* — Victoria Hicks Fisher

(57) ABSTRACT

A method of treating snoring among two users includes determining that snoring by at least one of the users is occurring, and responsive thereto, either: (a) determining that only one of the at least two users is snoring and responsive thereto generating a signal to produce an antisnoring motion in an active pillow associated with the one user and generating another signal to produce a distracting motion in another active pillow associated with the other user; or (b) determining that both of the users are snoring and responsive thereto generating signals to produce antisnoring motions in each of the active pillows.

4 Claims, 4 Drawing Sheets

(58) Field of Classification Search
USPC .......................................................... 128/848
See application file for complete search history.

(56) References Cited

U.S. PATENT DOCUMENTS

| | | |
|---|---|---|
| 2004/0234080 A1 | 11/2004 | Hernandez et al. |
| 2009/0094750 A1 | 4/2009 | Oguma et al. |
| 2012/0163626 A1 | 6/2012 | Booij et al. |
| 2012/0220888 A1 | 8/2012 | Wolfe et al. |
| 2015/0157519 A1 | 6/2015 | Stusynski et al. |
| 2015/0320588 A1* | 11/2015 | Connor ................. A61F 7/0085 607/104 |
| 2017/0053637 A1* | 2/2017 | DeFranks ........ G10K 11/17817 |
| 2021/0353082 A1* | 11/2021 | Lin ........................... A61F 5/56 |

OTHER PUBLICATIONS

International Search Report and Written Opinion, International Application No. PCT/EP2017/084219, dated Apr. 9, 2018.

* cited by examiner

SYSTEM FOR TREATING SNORING AMONG AT LEAST TWO USERS

CROSS-REFERENCE TO PRIOR APPLICATIONS

This application is the U.S. National Phase application under 35 U.S.C. § 371 of International Application Serial No. PCT/EP2017/084219, filed on 21 Dec. 2017, which claims the benefit of U.S. Application Ser. No. 62/438,485, filed on 23 Dec. 2016. These applications are hereby incorporated by reference herein.

BACKGROUND OF THE INVENTION

1. Field of the Invention

The present invention pertains to systems for treating snoring among at least two users. The present invention also pertains to methods for treating snoring among at least two users.

2. Description of the Related Art

Snoring is a concern for those suffering from the condition as snoring can result in low quality sleep and frequent awakenings. Snoring is also not only a concern for snorers themselves, but a major source of annoyance for the bed partners of those who frequently snore. Hence snoring has a significant effect on the sleep quality of both the snorer and the bed partner.

There are various classes of anti-snoring devices commercially available that address different types of snoring, originated from different source locations; e.g. nasal, palatal, back of the tongue, etc. Active anti-snoring pillows are one of the anti-snoring device categories which are commercially available. The effective mechanism of an active anti-snoring pillow is to change the position of the head of snorer (e.g., without limitation, by a mild rocking motion).

Active anti-snoring pillows are a good example of an unobtrusive intervention to snoring problem. They typically act by inducing a rocking motion that helps to shift the head position and thus disrupt snoring, ideally without waking the snorer. While such active pillows are generally effective for snoring with a positional nature, their effectiveness decreases for multifactorial snoring, as well as snoring induced by seasonal changes (e.g. due to nasal congestion). As a result, active anti-snoring pillows typically cannot provide a complete elimination of snoring. Residual snoring, even though it has reduced to a lower level, still induces sleep disorders for the bed partners of snorers.

Another problem with existing solutions is the adherence to the use of the anti-snoring pillow, especially in the presence of residual snoring, despite potential improvements provided on the snoring level and prevalence.

As expected, these problems get more complicated in cases where both bed partners are snoring. For example, yet another problem is related to the nature of commercially available active anti-snoring pillow solutions: they typically contain a means (e.g., an acoustic sensor) for detecting snoring for triggering the active mechanical motion. However, in cases where either bed partner may be snoring, the system has a high risk of inducing an irrelevant action as a non-snoring partner may have their active pillow activated by the snoring of their partner who is lying nearby.

SUMMARY OF THE INVENTION

In one embodiment, a method of treating snoring among at least two users is provided. Each user has a respective active pillow associated therewith. Each active pillow has a mechanism which produces at least two distinct motions: an anti-snoring motion which manipulates the head of a user thereof in a manner which reduces snoring and a distracting motion which manipulates the head of a user thereof in a manner which reduces noticeability of snoring by another user. The method comprises: determining that snoring by at least one of the at least two users is occurring; and responsive thereto, either: (a) determining that only one of the at least two users is snoring and responsive thereto: generating one signal to produce the anti-snoring motion in the active pillow associated with the one user, and generating another signal to produce the distracting motion in the active pillow associated with the other user; or (b) determining that both of the users are snoring and responsive thereto generating signals to produce the anti-snoring motion in each of the active pillows.

Determining that only one or that both of the users is snoring may comprise performing an acoustic analysis.

The method may further comprise: communicating the signal to produce the anti-snoring motion to a controller disposed in the active pillow associated with the one user; and communicating the signal to produce the distracting motion to a controller disposed in the active pillow associated with the other user.

Communicating the signal to produce the anti-snoring motion and communicating the signal to produce the distracting motion may comprise wirelessly communicating the signals.

The method may further comprise: producing the anti-snoring motion with the mechanism in the active pillow associated with the one user; and producing the anti-snoring motion with the mechanism in the active pillow associated with the other user.

One of communicating the signal to produce the anti-snoring motion and communicating the signal to produce the distracting motion may comprise wirelessly communicating the signal; and the other of one of communicating the signal to produce the anti-snoring motion and communicating the signal to produce the distracting motion may comprise communicating the signal via a wired connection.

The method may further comprise: producing the anti-snoring motion with the mechanism in the active pillow associated with the one user; and producing the anti-snoring motion with the mechanism in the active pillow associated with the other user.

In another embodiment, a control system for use in treating snoring among at least two users is provided. Each user has a respective active pillow associated therewith. Each active pillow has a mechanism which produces at least two distinct motions: an anti-snoring motion which manipulates the head of a user thereof in a manner which reduces snoring, and a distracting motion which manipulates the head of a user thereof in a manner which reduces noticeability of snoring by another user. The control system comprises: a sensing system structured to detect snoring by at least one of the users; and a processing unit in communication with the sensing system, the processing unit programmed to determine, from a communication with the sensing system, that snoring by at least one of the at least two users is occurring; and either: (a) determine that only one of the at least two users is snoring and responsive thereto: generate a signal to produce the anti-snoring motion in the active pillow associated with the one user, and generate another signal to produce the distracting motion in the active pillow associated with the other user; or (b)

determine that both of the users are snoring and responsive thereto generate signals to produce the anti-snoring motion in each of the active pillows.

The control unit may further comprise a transmitting device in communication with the processing unit, the transmitting device structured to transmit the signals generated by the processing unit.

In yet another embodiment, a system for use in treating snoring from among at least two users is provided. The system comprises: at least two active pillows, each active pillow associated with a respective user, each active pillow having a mechanism which produces at least two distinct motions: an anti-snoring motion which manipulates the head of a user thereof in a manner which reduces snoring and a distracting motion which manipulates the head of a user thereof in a manner which reduces noticeability of snoring by another user; and a control system comprising: a sensing system structured to detect snoring by at least one of the users; and a processing unit in communication with the sensing system, the processing unit programmed to determine, from a communication with the sensing system, that snoring by at least one of the at least two users is occurring; and either: (a) determine that only one of the at least two users is snoring and responsive thereto: generate a signal to produce the anti-snoring motion in the active pillow associated with the one user, and generate another signal to produce the distracting motion in the active pillow associated with the other user; or (b) determine that both of the users are snoring and responsive thereto generate signals to produce the anti-snoring motion in each of the active pillows.

The system may further comprise a transmitting device in communication with the processing unit, the transmitting device structured to wirelessly transmit the signals generated by the processing unit.

In yet a further embodiment, a computer program product including a non-transitory computer readable medium encoded with a computer program comprising program code for implementing the methods described herein is provided.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
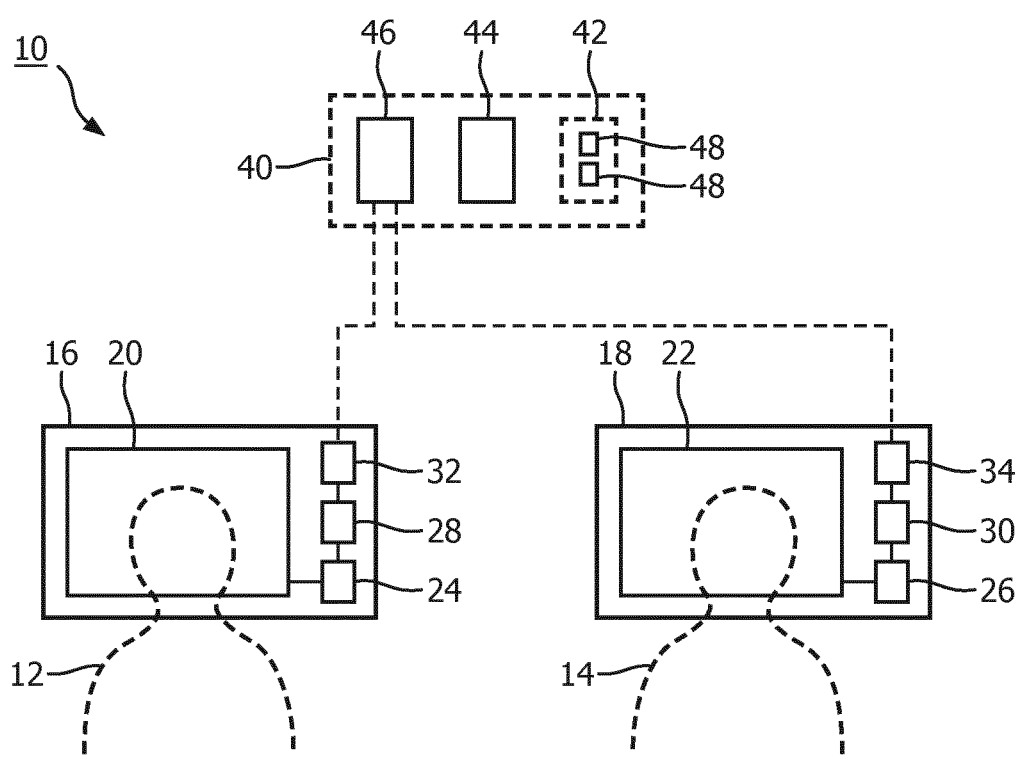
FIG. 1 is a schematic diagram of a system for treating snoring among at least two users according to one exemplary embodiment of the present invention.

As used herein, the singular form of "a", "an", and "the" include plural references unless the context clearly dictates otherwise.

As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the term "snoring" shall refer to the undesired occurrence of vibration of respiratory structures and the resulting sound due to obstructed air movement in a user during breathing while sleeping.

As used herein, the term "active pillow" shall be used to refer to a pillow for use by a user when sleeping. Such an "active pillow" includes one or more mechanisms which are positioned and structured to selectively move the head of the user in a predetermined manner. Such selective movements include, at minimum, a first movement (i.e., "an anti-snoring movement") which would tend to reduce and/or eliminate snoring by a user. In one example embodiment, a gentle rocking motion has been found to be effective, however other suitable motions may be employed without varying from the scope of the present invention. Such selective movements also include, at minimum, a second movement (i.e., a "distracting movement"), different from the first movement, which would tend to distract a non-snoring user from another user who is snoring and encourage the non-snoring user to remain, or fall back, asleep. In one example embodiment, an up-down motion has been found to be effective, however other suitable motions may be employed without varying from the scope of the present invention.

As used herein, the term "controller" or "processing device" shall mean a programmable analog and/or digital device (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the terms "receiver", "transmitter" and "transceiver" shall be used to describe devices which are structured, at minimum, to receive, transmit, or both, respectively, wireless signals via any wireless transmission arrangement (e.g., without limitation, WiFi, Bluetooth, etc.).

A system 10 for use in treating snoring from among at least two users 12, 14 (each shown in dashed line) in accordance with an example embodiment of the present invention is illustrated schematically in FIG. 1. System 10 includes at least two active pillows (i.e., a first active pillow 16 and a second active pillow 18), with each active pillow 16, 18 associated with a respective user 12, 14 such that the head (not numbered) of each user 12, 14 is disposed generally thereon. Each active pillow 16, 18 includes a suitable mechanism 20, 22 which is structured to produce at least two distinct motions. One of such distinct motions is an anti-snoring motion (previously discussed) which manipulates the head of the user thereof in a manner which reduces and/or eliminates snoring by a user thereof. Another of such distinct motions is a distracting motion (previously discussed) which manipulates the head of the user thereof in a manner which reduces noticeability of snoring by another user.

Each active pillow 16, 18 further includes an actuator 24, 26 operatively coupled (e.g., via mechanical, pneumatic, or other suitable means) to mechanism 20, 22 such that actuator 24, 26 can actuate mechanism 20, 22 to perform the at least two distinct motions previously discussed. A controller 28, 30 is electrically connected to actuator 24, 26 as well as to a wireless receiver 32, 34. Controller 28, 30 is structured to produce one or more signals, which control actuator 24, 26, in response to receiving one or more predetermined wireless signals via receiver 32, 34. Although shown as separate components, it is to be appreciated that one or more of mechanism 20, 22; actuator 24, 26; controller 28, 30; and/or receiver 32, 34 may be generally combined to form one or more elements which provide multiple functions such as described herein without varying from the scope of the present invention.

System 10 further includes a control system 40 which is shown in dashed line in FIG. 1 as the components thereof may be provided in a single unit or may be provided in multiple units, as will be discussed further herein. Control system 40 includes a sensing system 42, a processing unit 44 in communication with sensing system 42, and a wireless transmitter 46 which is also in communication with processing unit 44. Similar to control system 40, sensing system 42 is also shown in dashed line as the components thereof may be provided in a single unit or may be provided in multiple units, as will be discussed further herein. Sensing system 42 includes a number (two are shown in the example) of acoustic sensors 48 which are structured to detect environmental sounds in the vicinity of users 12, 14 and communicate (either via a wired or wireless connection depending on the application) data related to such detected sounds to processing unit 44. Depending on the placement of sensors 48 (e.g., without limitation, in the pillow, on the bedside, another location in the bedroom, etc.), they can be selected as omnidirectional, directional, or contact microphones. The dynamic range and the spectrum of sensors 48 should be selected according to the snoring sound spectrum, and by considering the acoustic signal attenuation, for example in case of placement within the pillow tissue, and/or a bedside monitoring unit. Acquired acoustic signals are expected to be conditioned and processed for providing sufficient selectivity for snoring.

Processing unit 44 is structured to utilize data gathered by sensing system 42 along with a suitable algorithm (stored in a memory associated with processing unit 44) to perform an acoustic analysis in order to determine if such sounds constitute snoring, and from which or both users is the snoring emanating, and potentially send one or more signals (as will be discussed below) via transmitter 46 to one or both of active pillows 16,18.

Having thus described a general overview of a system 10 in accordance with an example embodiment of the present invention, an example method 100, in accordance with the present invention, for treating snoring among at least two users, which may employ a system 10 will now be described in conjunction with the flow chart illustrated in FIG. 2. Method 100 begins at 102 wherein an acoustic analysis is performed in order to determine if snoring by one or both of users 12 and 14 is occurring. As previously discussed, such analysis may be carried out by processing unit 44 analyzing data (via a suitable algorithm) received from sensing system 42 to determine if snoring, by either or both of users 12, 14, is occurring, such as shown at 104. If it is determined at 104 that no snoring is occurring, then no action is taken aside from further acoustic analysis, such as shown at 102. If at 104 it is determined that snoring is occurring, further analysis is carried out by processing unit 44 at 106 to determine if the snoring is: emanating only from user 12 who is associated with (i.e., sleeping with their head on) first active pillow 16 (i.e., "pillow A" in FIG. 2); emanating only from user 14 who is associated with (i.e., sleeping with their head on) second active pillow 18 (i.e., "pillow B" in FIG. 2); or is emanating from both users 12 and 14. The determination of the snorer can be done in various ways; from simple sound amplitude comparison between two sides of the bed, to more complex approaches that involve acoustic feature extraction for resolving room acoustics; such as acoustic mapping of the ambient by using the input of multiple acoustic sensors (e.g. acoustic sensor arrays).

If it is determined at 106 that the snoring is emanating only from the user associated with first active pillow 16 (i.e., user 12), as shown at 108, a signal is generated by processing unit 44 (and communicated therefrom by transmitter 46 to receiver 32, controller 28 and actuator 24 of active pillow 16) which causes mechanism 20 to produce an anti-snoring motion (such as previously discussed) in active pillow 16. As also shown at 108, another signal is generated (either concurrently or in immediate proximity to the previously described signal) by processing unit 44 (and communicated therefrom by transmitter 46 to receiver 34, controller 30 and actuator 26 of active pillow 18) which causes mechanism 22 to produce a distracting motion (such as previously discussed) in active pillow 18. Hence, in such case system 10, utilizing method 100, serves to reduce and/or eliminate snoring by user 12 while minimizing any disturbance to user 14.

If it is determined at 106 that the snoring is emanating only from the user associated with second active pillow 18 (i.e., user 14), as shown at 110, a signal is generated by processing unit 44 (and communicated therefrom by transmitter 46 to receiver 34, controller 30 and actuator 26 of active pillow 18) which causes mechanism 22 to produce an anti-snoring motion (such as previously discussed) in active pillow 18. As also shown at 110, another signal is generated (either concurrently or in immediate proximity to the previously described signal) by processing unit 44 (and communicated therefrom by transmitter 46 to receiver 32, controller 28 and actuator 24 of active pillow 16) which causes mechanism 20 to produce a distracting motion (such as previously discussed) in active pillow 16. Hence, in such case system 10, utilizing method 100, serves to reduce and/or eliminate snoring by user 14 while minimizing any disturbance to user 12.

If it is determined at 106 that the snoring is emanating from both users 12 and 14, as shown at 112, a signal is generated by processing unit 44 (and communicated therefrom by transmitter 46 to receiver 32, controller 28 and actuator 24 of active pillow 16) which causes mechanism 20 to produce an anti-snoring motion (such as previously discussed) in active pillow 16. As also shown at 112, another signal is generated (either concurrently or in immediate proximity to the previously described signal) by processing unit 44 (and communicated therefrom by transmitter 46 to receiver 34, controller 30 and actuator 26 of active pillow 18) which causes mechanism 22 to also produce an anti-snoring motion (such as previously discussed) in active pillow 18. Hence, in such case system 10, utilizing method 100, serves to reduce and/or eliminate snoring by both users 12 and 14.

Regardless of the determination made at 106, another acoustic analysis, such as shown at 102 and previously discussed, is carried out after the actuations of mechanisms 20 and 22 are carried out in any of 108, 110, or 112 and the steps previously described are repeatedly carried out as needed throughout the sleeping time of users 12 and 14. Accordingly, it is to be appreciated that embodiments of the present invention provide a solution which treats snoring among at least two users in a novel manner.

Figure 2:
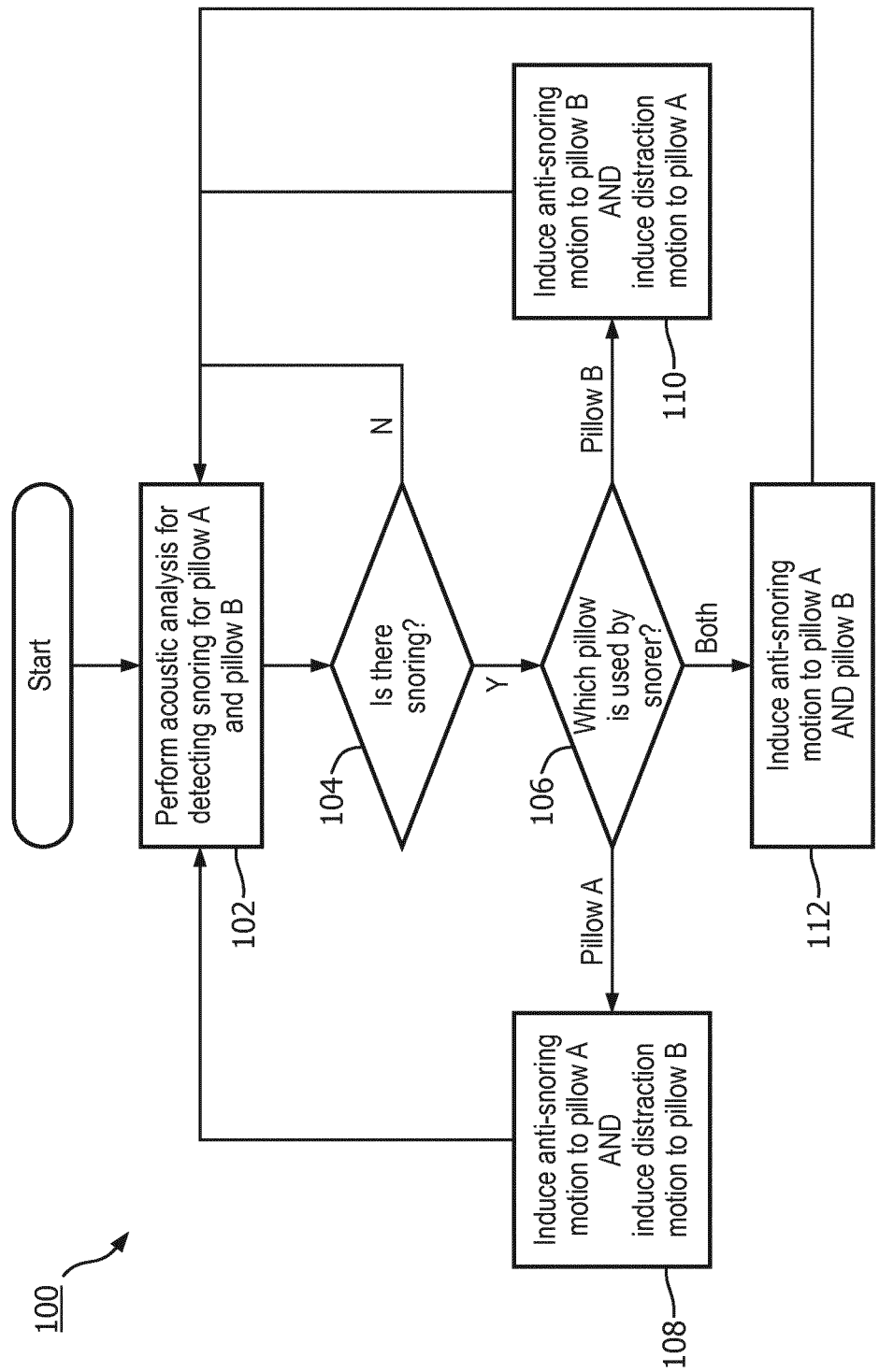
FIG. 2 is a flow diagram of a method according to one exemplary embodiment of the present invention.
Figure 3:
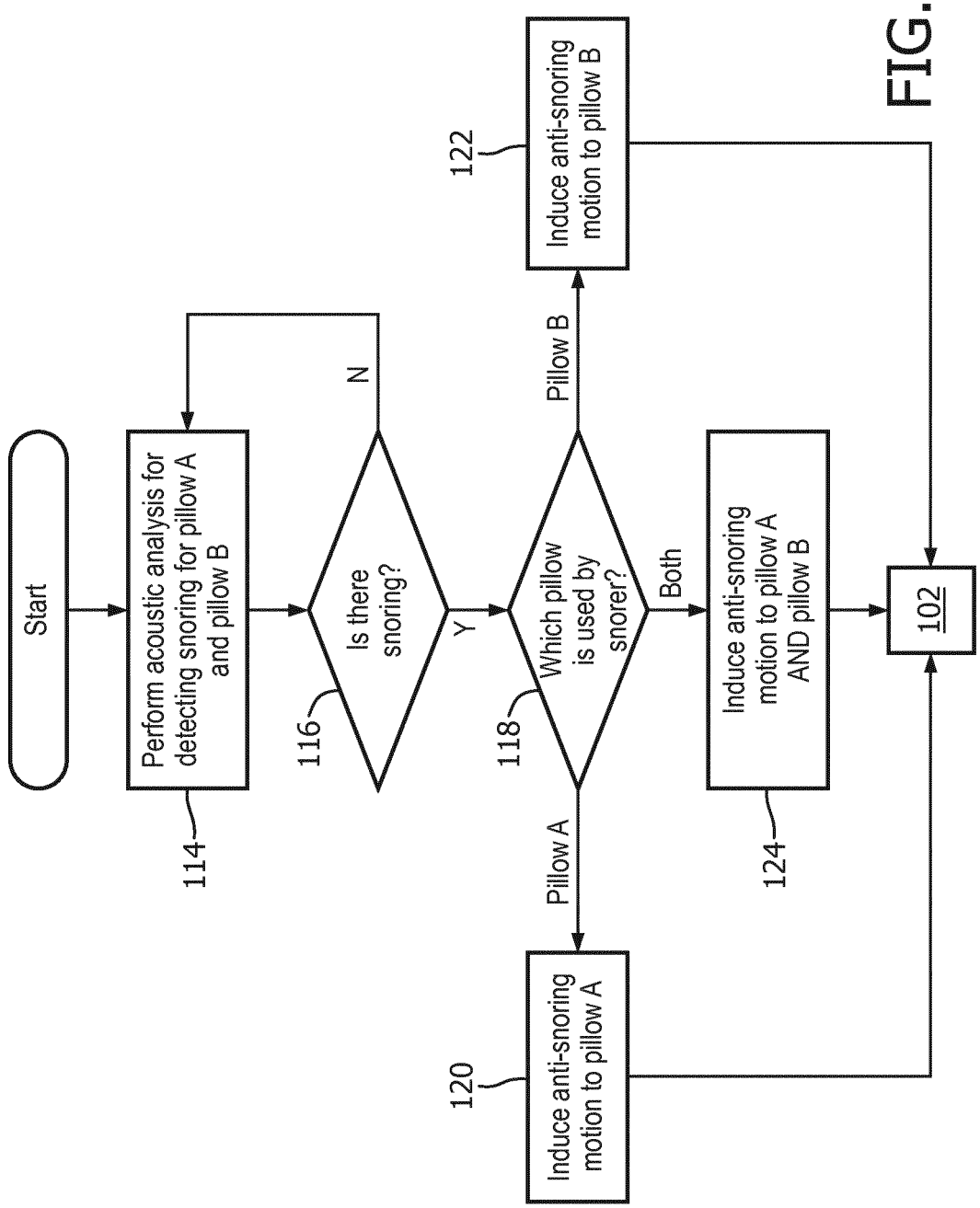
FIG. 3 is a flow diagram of a group of steps which may be carried out either independently or as an initial portion of the method of FIG. 3.

FIG. 3 shows a flow chart with a number of steps which may be carried out as a portion of method 100, prior to the steps previously discussed in conjunction with FIG. 2, or which may be carried out without the steps of method 100. Such steps begin at step 114 wherein an acoustic analysis is performed in order to determine if snoring by one or both of users 12 and 14 is occurring. As previously discussed, such analysis may be carried out by processing unit 44 analyzing data (via a suitable algorithm) received from sensing system 42 to determine if snoring, by either or both of users 12, 14, is occurring, such as shown at 118. If it is determined at 116 that no snoring is occurring, then no action is taken aside from further acoustic analysis, such as shown at 114. If at 116 it is determined that snoring is occurring, further analysis is carried out by processing unit 44 at 118 to determine if the snoring is: emanating only from user 12 who is associated with (i.e., sleeping with their head on) first active pillow 16 (i.e., "pillow A" in FIG. 2); emanating only from user 14 who is associated with (i.e., sleeping with their head on) second active pillow 18 (i.e., "pillow B" in FIG. 2); or is emanating from both users 12 and 14. The determination of the snorer can be done in various ways; from simple sound amplitude comparison between two sides of the bed, to more complex approaches that involve acoustic feature extraction for resolving room acoustics; such as acoustic mapping of the ambient by using the input of multiple acoustic sensors (e.g. acoustic sensor arrays).

If it is determined at 118 that the snoring is emanating only from the user associated with first active pillow 16 (i.e., user 12), as shown at 120, a signal is generated by processing unit 44 (and communicated therefrom by transmitter 46 to receiver 32, controller 28 and actuator 24 of active pillow 16) which causes mechanism 20 to produce an anti-snoring motion (such as previously discussed) in active pillow 16 (i.e., "Pillow A" of FIG. 3), while no action is taken in regard to active pillow 18 (i.e., "Pillow B" of FIG. 3).

If it is determined at 118 that the snoring is emanating only from the user associated with second active pillow 18 (i.e., user 14), as shown at 122, a signal is generated by processing unit 44 (and communicated therefrom by transmitter 46 to receiver 34, controller 30 and actuator 26 of active pillow 18) which causes mechanism 22 to produce an anti-snoring motion (such as previously discussed) in active pillow 18 (i.e., "Pillow B" of FIG. 3), while no action is taken in regard to active pillow 16 (i.e., "Pillow A" of FIG. 3).

If it is determined at 118 that the snoring is emanating from both users 12 and 14, as shown at 124, a signal is generated by processing unit 44 (and communicated therefrom by transmitter 46 to receiver 32, controller 28 and actuator 24 of active pillow 16) which causes mechanism 20 to produce an anti-snoring motion (such as previously discussed) in active pillow 16. As also shown at 124, another signal is generated (either concurrently or in immediate proximity to the previously described signal) by processing unit 44 (and communicated therefrom by transmitter 46 to receiver 34, controller 30 and actuator 26 of active pillow 18) which causes mechanism 22 to also produce an anti-snoring motion (such as previously discussed) in active pillow 18.

Regardless of the determination made at 118, the acoustic analysis described in step 102 of FIG. 3 is then performed after the actuations of mechanisms 20 and 22 are carried out in any of 120, 122, or 124. After step 102 is performed, the method continues with the remainder of the steps of method 100 as described in conjunction with FIG. 3. It is to be appreciate that the additional preliminary steps described in conjunction with FIG. 3 provide for a method which makes an initial attempt to address snoring by at least one of the users without initially doing anything to the non-snoring user. However, if the snoring is not eliminated after the initial attempt, the non-snoring user is then also addressed (as generally described in method 100).

It is to be appreciated that the methods described herein may be implemented in by a computer program product including a non-transitory computer readable medium encoded with a computer program comprising program code (for implementing the methods).

Figure 4:
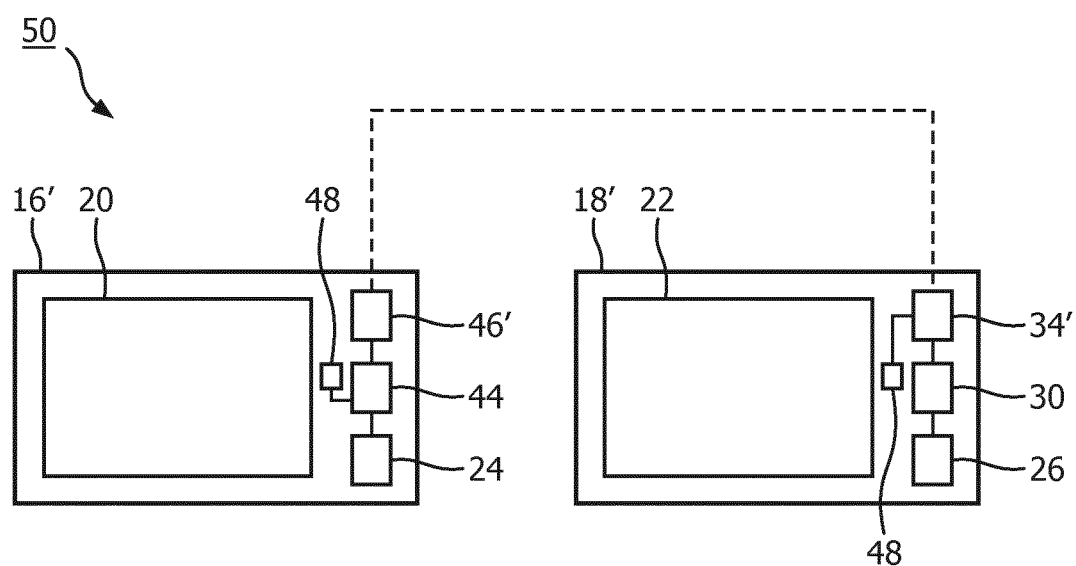
FIG. 4 is a schematic diagram of a system for treating snoring among at least two users according to another exemplary embodiment of the present invention.

An example embodiment of a system 50 in accordance with another example embodiment of the present invention is schematically illustrated in FIG. 4. System 50 includes similar components (commonly numbered) as system 10 previously discussed. However, system 50 provides an example arrangement in which the components of control system 40 (i.e., acoustic sensors 48, processing unit 44, and transmitter 46) have been generally incorporated into active pillows 16' and 18'. More particularly, system 50 includes a first active pillow 16' which includes processing unit 44 which is in communication with actuator 24, an acoustic sensor 48, and a transceiver 46'. System 50 further includes a second active pillow 18' which includes controller 30 which is in communication with actuator 26 and a transceiver 34'. Pillow 18' also includes an acoustic sensor 48 which is in communication with transceiver 34'. Transceiver 34' is structured to wirelessly communicate data received from acoustic sensor 48 to processing unit 44 (via transceiver 46'). Transceiver 34' is also structured to wirelessly receive signals from processing unit 44 (via transceiver 46') and communicate such signals to controller 30 and actuator 26, which can then cause mechanism 22 to be actuated accordingly. Processing unit 44 is in direct communication with actuator 24, which can cause mechanism 20 to be actuated accordingly.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. As another example, it is to be appreciated that although described in embodiment in which only a user's head is manipulated, other movements of portions or the entirety of the users which serve to minimize snoring and/or help to distract/soothe a user may be employed without varying from the scope of the present invention. Also, additional features (e.g., without limitation, sound, heating, cooling) may be used without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A control system for use in treating snoring among at least two users, the control system comprising:
   a sensing system structured to detect snoring by at least one of the at least two users; and
   a processing device in communication with the sensing system, the processing device programmed to determine, from a communication with the sensing system, that snoring by at least one of the at least two users is occurring; and
   either:
      (a) determine that only one of the at least two users is snoring and responsive thereto:
         generate a signal to produce an anti-snoring motion in an active pillow associated with the one of the at least two users, wherein the anti-snoring motion is capable of manipulating the head of the respective user in a manner which reduces snoring, and
         generate another signal to produce a distracting motion in another active pillow associated with another user of the at least two users, wherein the distracting motion is capable of manipulating the head of the respective user in a manner which reduces noticeability of snoring; or
      (b) determine that both of the users of the at least two users are snoring and responsive thereto generate signals to produce the anti-snoring motion in each of the active pillows.

2. The control system of claim 1, further comprising a transmitter in communication with the processing device, the transmitter structured to transmit the signals generated by the processing device.

3. A system for use in treating snoring from among at least two users, the system comprising:
   at least two active pillows, each active pillow structured to be associated with a respective user; and
   a control system comprising:
      a sensing system structured to detect snoring by at least one of the at least two users; and
      a processing device in communication with the sensing system, the processing device programmed to determine, from a communication with the sensing system, that snoring by at least one of the at least two users is occurring; and
   either:
      (a) determine that only one of the at least two users is snoring and responsive thereto:
         generate a signal to produce an anti-snoring motion in the active pillow associated with the one of the at least two users, wherein the anti-snoring motion is capable of manipulating the head of the respective user in a manner which reduces snoring, and
         generate another signal to produce a distracting motion in the active pillow associated with another user of the at least two users, wherein the distracting motion is capable of manipulating the head of the respective user in a manner which reduces noticeability of snoring; or
      (b) determine that both of the at least two users are snoring and responsive thereto generate signals to produce the anti-snoring motion in each of the active pillows.

4. The system of claim 3, further comprising a transmitter in communication with the processing device, the transmitter structured to transmit the signals generated by the processing device.

* * * * *